United States Patent
Yamamoto et al.

(10) Patent No.: US 6,480,274 B1
(45) Date of Patent: Nov. 12, 2002

(54) METHOD OF ANALYZING OXYGEN AND OXIDE IN METALLIC MATERIAL

(75) Inventors: Akira Yamamoto, Chiba (JP); Wataru Tanimoto, Okayama (JP)

(73) Assignee: Kawasaki Steel Corporation, Hyogo (JP)

( * ) Notice: Subject to any disclaimer, the term of this patent is extended or adjusted under 35 U.S.C. 154(b) by 0 days.

(21) Appl. No.: 09/446,530

(22) PCT Filed: Apr. 28, 1999

(86) PCT No.: PCT/JP99/02292

§ 371 (c)(1),
(2), (4) Date: Dec. 28, 1999

(87) PCT Pub. No.: WO99/56110

PCT Pub. Date: Nov. 4, 1999

(30) Foreign Application Priority Data

Apr. 28, 1998 (JP) .......................................... 10-118065
Apr. 28, 1998 (JP) .......................................... 10-118066

(51) Int. Cl.[7] .............................................. G01N 21/67
(52) U.S. Cl. ...................................... 356/313; 356/307
(58) Field of Search .................................. 356/307, 313

(56) References Cited

U.S. PATENT DOCUMENTS

| 4,255,051 A | 3/1981 | Imamura et al. ............. 356/313 |
| 4,326,801 A | 4/1982 | Ono et al. .................... 356/313 |
| 4,592,655 A | 6/1986 | Slickers ....................... 356/313 |
| 4,732,478 A | 3/1988 | Willay et al. ................ 356/313 |

FOREIGN PATENT DOCUMENTS

| EP | 0 501 476 A2 | 9/1992 |
| EP | 0 504 933 A2 | 9/1992 |
| EP | 0 504 933 A3 | 9/1992 |
| EP | 0 780 677 A1 | 6/1997 |
| JP | 3-295449 | 12/1991 |
| JP | 4-294258 | 10/1992 |
| JP | 5-223739 | 8/1993 |
| JP | 5-273128 | 10/1993 |
| JP | 6-337245 | 6/1994 |

Primary Examiner—F. L. Evans
(74) Attorney, Agent, or Firm—Young & Thompson

(57) ABSTRACT

This invention provides a quantitative determination method capable of quickly determining a mean composition of oxide type inclusions and oxygen concentration of a metallic material such as a steel by using an optical emission spectrometer alone. This method comprises the steps of (1) conducting a plurality of times a discharge operation between the metallic material and an opposing electrode in an inert gas atmosphere to obtain an emission spectrochemical spectrum, (2) selecting a discharge in which at least either the oxygen A spectrum or the oxide-forming element spectrum exceed a predetermined intensity for each discharge operation, and (3) subtracting a background from the intensity of the oxygen spectrum and/or the intensity of the oxide-forming elements in the selected discharge, accumulating the balances to obtain a cumulative spectral intensity, and executing quantitative determination by a calibration curve method.

10 Claims, 6 Drawing Sheets

METHOD OF ANALYZING OXYGEN AND OXIDE IN METALLIC MATERIAL

TECHNICAL FIELD

This invention relates to a method of rapid and highly accurate analysis of oxygen and oxides that are contained in a metallic material by an optical emission spectroscopic analysis. More particularly, this invention relates to a quick and efficient analytical technology for quantitative determination of oxygen and/or the mean composition of oxides contained in a metallic material such as a steel material.

BACKGROUND ART

Oxides and so-called "oxide-type inclusions", if contained in a steel material, greatly affect quality characteristics of the steel material such as the formation process characteristics of the steel material and its surface property. Therefore, when the steel material is molten, these oxides are controlled as the oxygen concentration of the molten steel is analyzed and is regulated to be in a predetermined concentration range.

A combustion-infrared absorption method has been generally employed at present as a quantitative determination method of this oxygen concentration. In other words, molten steel collected from a converter or a secondary refining furnace such as a VOD or an RH is solidified first in a mold to obtain an analytical specimen having a predetermined size. The specimen so obtained is loaded into a carbon crucible, and is heat-molten in an inert gas atmosphere. Oxygen dissociates from the oxides inside the specimen during this melting process, reacts with carbon of the crucible and generates a carbon dioxide gas. The oxygen concentration in the steel can be quantitatively determined as the quantity of carbon dioxide is measured by infrared absorption.

On the other hand, an optical emission spectroscopic analysis capable of analyzing simultaneously and quickly multiple elements has been employed for a process control analysis of a steel making process in order to analyze element concentrations of the metal specimen. This optical emission spectroscopic analysis executes a discharge operation a plurality of times between the metal specimen and an opposing electrode in an inert gas atmosphere, analyzes spectrally the spectrum inherent to each element generated by the discharge, and quantitatively determines each element concentration in the metal specimen from the intensity of each spectrum.

In the quantitative determination of the oxygen concentration in the steel by this optical emission spectroscopic analysis, however, emission spectra from trace amounts of moisture and oxygen of air that are contained in the discharge gas form a large background to the emission spectrum of oxygen as the object of the analysis from the metal specimen. In consequence, a signal-to-noise ratio (S/N) is low and accuracy of quantitative determination of oxygen is not sufficient, so that the optical emission spectroscopic analysis cannot be put into practical application. In the process control analysis of the steel making process described above, therefore, the analysis of only oxygen is conducted by the combustion-infrared absorption method described above. Therefore, excessive equipment and analysis time are necessary, and they present a problem in both economy and process management.

Quantitative determination by optical emission spectroscopic analysis can keep the accuracy of the determination of those inclusion elements which are substantially solid and insoluble such as Ca and Mg to a predetermined level. When the elements have high solid solubility such as Al, Si, Mn, Ni, Cr, and the like, however, it becomes difficult to distinguish the resulting spectral intensity originating from the solid solution elements from the spectral intensity from the solid insoluble elements. In consequence, accuracy of quantitative determination greatly relies on the skill or experience of analyzing engineers, and the problem of steadiness remains unsolved.

Further, the optical microscope observation method is one of the methods of evaluating the inclusions in the steel. This method observes a mirror-polished specimen through an optical microscope and counts the number of the inclusions contained in the specimen with eye. However, this method requires one- or two-days of time for the preparation of the specimen and for the measurement, lacks quickness, and cannot determine quantitatively the composition of the inclusions because the method is an inspection method of cleanness with eye.

Another evaluation method identifies the inclusions in the steel with an electron probe micro-analyzer (EPMA) or an electron microscope. However, this method not only requires a long time for polishing as a pre-treatment of the specimen but complicated procedures for the operation of equipment and various processing. Though this method can quantitatively determine the composition, it lacks quickness of measurement and cannot analyze quickly large quantities of specimens.

An extraction separation—ICP (inductively coupled plasma) atomic emission spectroscopic analysis has been employed in recent years as a composition analysis method of the inclusions in the steel. This method chemically extracts the oxides by dissolving the specimen in an acid or halogen solution, further dissolves the oxides obtained as the extraction residue and analyzes the composition by the ICP optical emission spectroscopic analysis. Because one- or two-days of time is necessary for the pre-treatment and the measurement of the specimen, this method lacks quickness of measurement and involves further the problem that the result of the analysis varies depending on the kind of the extracting solution selected.

As described above, a plurality of analyzing means have been used in combination with one another in the past depending on the object of analysis in the analysis of the oxygen concentration and/or the oxide composition of inclusions in the metallic specimen in order to keep a predetermined level of accuracy of quantitative determination. Because the analyzing time also varies from specimen to specimen, the result of analysis of all the data cannot be obtained before a long time of at least two days and the overall judgement is likely to get delayed. Consequently, all these methods are not free from the losses in both economy and time.

DISCLOSURE OF THE INVENTION

In view of the problems described above, the present invention provides a quantitative determination method capable of determining quickly and highly accurately a mean oxygen concentration in a metallic material and/or a mean inclusion composition by using, as analyzing means, only an optical emission spectrometer alone as a main analytical apparatus for the process control analysis of a steel making process.

To accomplish this object, the inventors of the present invention have paid specific attention to the form in which the elements are present in a metallic specimen and their spectral intensities obtained by emission spectroscopy, have examined their correlation, and have thus completed the present invention.

In other words, the present invention provides a method of quantitatively determining the mean oxygen concentration in a metallic material and/or the mean oxide-forming element concentration originating from oxides in the metallic material, which method comprises the steps of:

(1) conducting a discharge operation a plurality of times between the metallic material and an opposing electrode in an inert gas atmosphere to obtain an optical emission spectroscopic spectrum;

(2) selecting a discharge from the spectrum in which at least the oxide-forming element spectrum exceeds a predetermined intensity;

(3) subtracting a background from the intensity of the oxygen spectrum and/or the intensity of the oxide-forming element spectrum in the selected discharge, and accumulating the balances to obtain a cumulative spectrum intensity; and (4) executing quantitative determination by a calibration curve method.

The present invention provides also a method of quantitatively determining a mean oxide-forming element concentration originating from oxides in the metallic material described above, which method comprises the steps of:

(1) selecting a discharge in which an oxide-forming element spectrum and the oxygen spectrum exceed respective predetermined intensities;

(2) subtracting the predetermined intensity of the oxide-forming element as a background from the intensity of the oxide-forming element spectrum in the selected discharge, and accumulating the balances to obtain a cumulative spectral intensity of the oxide-forming elements; and (3) conducting quantitative determination using a separately prepared calibration curve of the average concentration of oxide-forming elements, comparing this to the above cumulative spectral intensity.

The present invention provides further a method of quantitatively determining a mean oxygen concentration in the metallic material described above, which method comprises the steps of:

(1) selecting a discharge in which the oxide-forming element spectrum exceeds a predetermined intensity;

(2) selecting oxygen spectra obtained at the time of the discharge so selected;

(3) determining a background of the oxygen spectrum, through the frequency distribution of the other oxygen spectra, using the intensity and the number of discharges;

(4) selecting again from among the oxygen spectra selected by the steps (2) the oxygen spectra having an intensity higher than the background;, (5) subtracting the background from the intensity of the oxygen spectrum selected again and accumulating the balances to obtain a cumulative spectral intensity of oxygen; and (6) conducting quantitative determination using a calibration curve, prepared separately from the oxygen concentration and the cumulative spectral intensity.

Incidentally, in either of the methods of quantitatively determining the mean oxygen concentration in the metallic specimen and/or the mean oxide-forming element concentration of oxides in the metallic material according to the present invention described above, the quantitative determination method preferably finds the intensity ratio of the spectral intensity of the element to be quantitatively determined to the spectral intensity of the matrix element of the metallic material.

In either of the cases whether the mean oxygen concentration in the metallic material and/or the mean oxide-forming element concentration originating from oxides in the metallic material is quantitatively determined, the predetermined reference intensity preferably employs at least one of the following; median value, mean value, or mean value+n×standard deviation (n: positive integer) in a frequency distribution of the spectral intensity of the element to be determined and the number of discharges, or in a frequency distribution of the spectral intensity ratio of the element to be determined to the matrix element.

The method of the present invention which quantitatively determines the mean oxygen concentration in the metallic material and/or the mean oxide-forming element concentration of oxides in the metallic material can be employed appropriately when the metallic material is iron.

BEST MODE FOR CARRYING OUT THE INVENTION

Hereinafter, the content of the present invention will be explained with the background of the invention.

In the optical emission spectroscopic analysis according to the present invention, a discharge operation is carried out a plurality of times. The number of times of such a discharge. operation is preferably great in order to acquire sufficient reliability as a mean concentration that is quantitatively determined, but is not limited, in particular. When the discharge depth into the specimen and ease of detection of the spectra are taken into consideration, however, the discharge operation is preferably, and generally, carried out 500 to 5,000 times and more preferably, 1,000 to 3,000 times.

Figure 1:
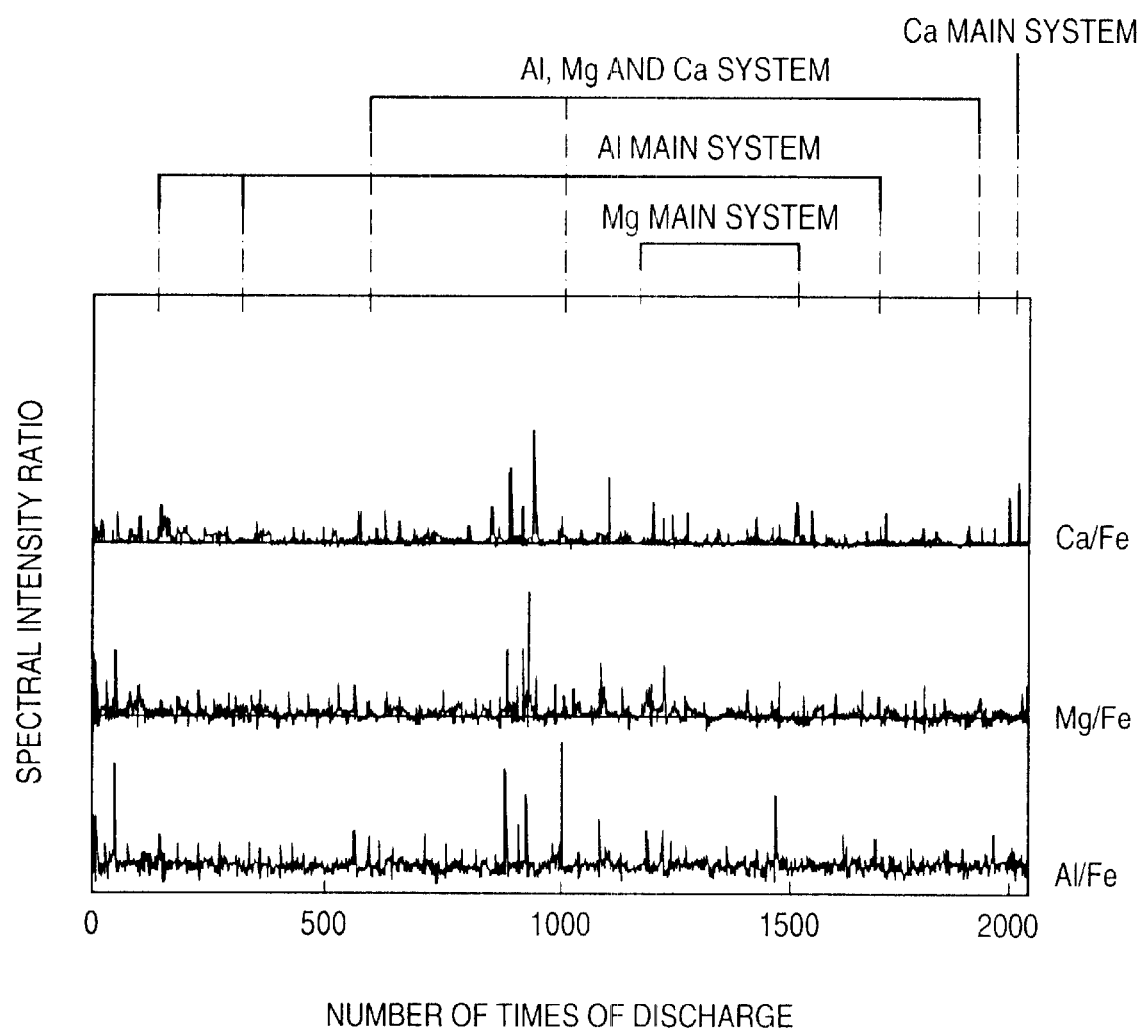
FIG. 1 is a graph showing typically the change of Al/Fe, Ca/Fe and Mg/Fe spectral intensity ratios for each discharge.

An optical emission spectroscopic analysis is conducted for the elements contained in a metallic material obtained by solidifying a molten steel collected from a converter or a secondary refining furnace, by way of example. Incidentally, discharge is conducted 2,000 times per analysis of the optical emission spectroscopic analysis of this steel specimen. Therefore, 2,000 spectral intensity values can be obtained for each element. The present invention executes a quantitative analysis quickly and highly accurately using such spectral intensities. In order to obtain higher accuracy of the quantitative determination, however, it is more preferred to use a spectral intensity of each element to be measured as an intensity ratio with respect to a spectral intensity of a metal matrix element. Therefore, the spectral intensity ratios of the oxide-forming elements to Fe as the matrix, such as Al/Fe, Ca/Fe and Mg/Fe, are calculated from the spectral intensity for each discharge, and they are used as the spectral intensity of the present invention for the following quantitative determination. The result is shown in FIG. 1. As can be clearly seen from FIG. 1, there is a discharge in which the intensity ratios of these oxide-forming elements exhibit high values, and the discharge is presumably occurred to these oxides.

Oxygen in the metallic specimen is believed to be found wholly in the oxides. Therefore, it can be assumed hereby that the spectral intensity of oxygen as the object of analysis can be reliably grasped if the discharge in which the spectral intensity ratio of the oxide-forming elements exhibits a high value is selected and the spectral intensity ratios of oxygen at this time are accumulated.

Figure 2:
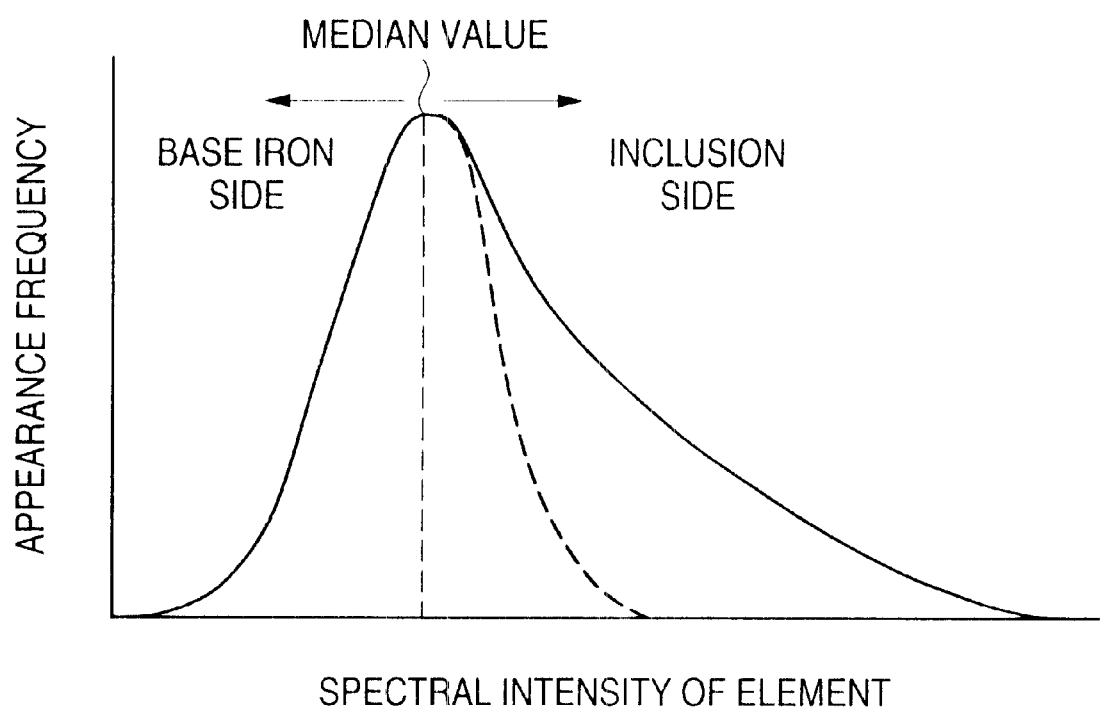
FIG. 2 is a graph showing typically a spectrum intensity of oxide-forming elements originating from oxides and a frequency distribution of discharges.

For this purpose, it is necessary to set a reference intensity for selecting the discharge in which the oxide-forming elements exhibit a high value (that is, a predetermined intensity). The inventors of the present invention employ the frequency distribution of the spectral intensity of the oxide-forming elements acquired by conducting a plurality of times the discharge operation for judgement. The spectral intensity ratios of Al, Si, Mn, etc, exhibit the frequency distribution shown in FIG. 2. The frequency distribution of the spectral intensity ratios of Al, Si, Mn, etc, is not symmetric with respect to the median value as shown in FIG. 2 for the following reasons. A part of the oxide-forming elements is not dissolved in Fe as the matrix element, but exists as an oxide. When discharge occurs to such an oxide, the spectral intensity of these elements in this discharge operation becomes relatively higher than when the discharge occurs to the base iron with the result that the frequency distribution is presumably shifted to a higher spectral intensity side. Therefore, the present inventors assume a dissolution region I (not shown in the drawing) into the matrix of the oxide-forming elements, in which the frequency distribution is symmetric, and a region II (not shown) in which the oxide-forming elements exist as the oxide.

Various reference values (that is, predetermined intensities) may be available for dividing these regions, but it would be reasonable to select and use the median value of the frequency distribution, the mean value or the [mean value +n×standard deviation (where n: positive integer)]. Among them, the median value can be used more generally, and can be used more appropriately for the oxygen analysis, for example. The mean value is preferably used for the oxygen analysis and for the composition analysis of oxide type inclusions inclusive of those having relatively small particle sizes. Furthermore, [mean value +n×standard deviation] is preferably used for the composition analysis of the oxide type inclusions having relatively large particle sizes. Incidentally, the value n in this case is preferably from 2 to 4.

The present invention executes the quantitative determination from the spectral intensity of oxygen in the discharge selected by the method described above.

However, this oxygen spectral intensity includes not only oxygen in the metallic specimen but also a trace amount of oxygen contained in the discharge gas due to the mixture of the open air or its adhesion to the specimen surface, or oxygen resulting from the moisture. Therefore, these kinds of oxygen are removed as so-called "background (BG)" so as to improve accuracy of quantitative determination.

More concretely, a discharge is chosen having an intensity lower than the reference value (predetermined intensity) described above from the frequency distribution of the spectral intensity ratios of the oxide-forming elements and the number of times of discharge operations, that is, the discharge to the base iron in which oxides do not exist. Next, suitable one of the median value, the mean value or [mean value+n×standard deviation] is suitably selected from the frequency distribution of the intensity ratio of the oxygen spectrum and the number of times of the discharge operations at the time of this discharge operation, and is set to be the background intensity ratio (BG) of oxygen. Therefore, the cumulative spectral intensity ratios of oxygen are determined by accumulating the difference obtained by subtracting this background intensity ratio from the oxygen spectral intensity ratio corresponding to the discharge operations in which the spectral intensity ratio of the oxide-forming elements exceed a predetermined value.

The operation described above is applied to a specimen the oxygen concentration of which is known in advance by the chemical analysis, and a calibration curve of an oxygen concentration—cumulative oxygen spectral intensity ratio is prepared. The oxygen concentration of the metallic specimen can be determined on the basis of this calibration curve.

Since the discharges in which the spectral intensity ratios of oxygen and oxide-forming elements exhibit high values are the discharges to the oxides, the inventors of the present invention assume that the concentrations of the oxide-forming elements in the oxide can be determined quantitatively from the spectral intensities of the oxide-forming elements at that time and the compositions of the oxides existing in the metallic specimen can be analyzed from the result so obtained.

In other words, in the frequency distribution of the spectral intensities of the oxide-forming elements described above, the afore-mentioned predetermined intensity can be regarded as the spectral intensity representative of the non-oxide concentration of free oxide-forming elements dissolved in the matrix. Therefore, the discharge operations in which oxygen and the oxide-forming elements exhibit intensity higher than the predetermined intensity are selected in the frequency distribution of the spectral intensities of oxygen and the oxide-forming elements, and the predetermined intensity is subtracted as the background (BG) from the spectral intensity of the oxide-forming elements in the selected discharge. The balances so obtained are accumulated and the cumulative spectral intensity of the oxide-forming elements is determined. In other words, the background at this time can be judged as resulting from the non-oxides such as the free oxide-forming elements.

The operation described above is applied to the specimen whose oxide-forming element concentration in the oxides is known in advance by the chemical analysis, and a calibration curve of the oxide-forming element concentrations originating from the oxides and the spectral intensity of the cumulative oxide-forming element spectral intensity is prepared. The concentrations of the oxide-forming elements in the oxides contained in the metallic specimen can be determined on the basis of the resulting calibration curve. The mean composition of the oxide can be analyzed appropriately when such an analysis is applied to so-called "solid soluble" oxide-forming elements such as Al, Si, Mn, Ni, Cr, and so forth.

Figure 6:
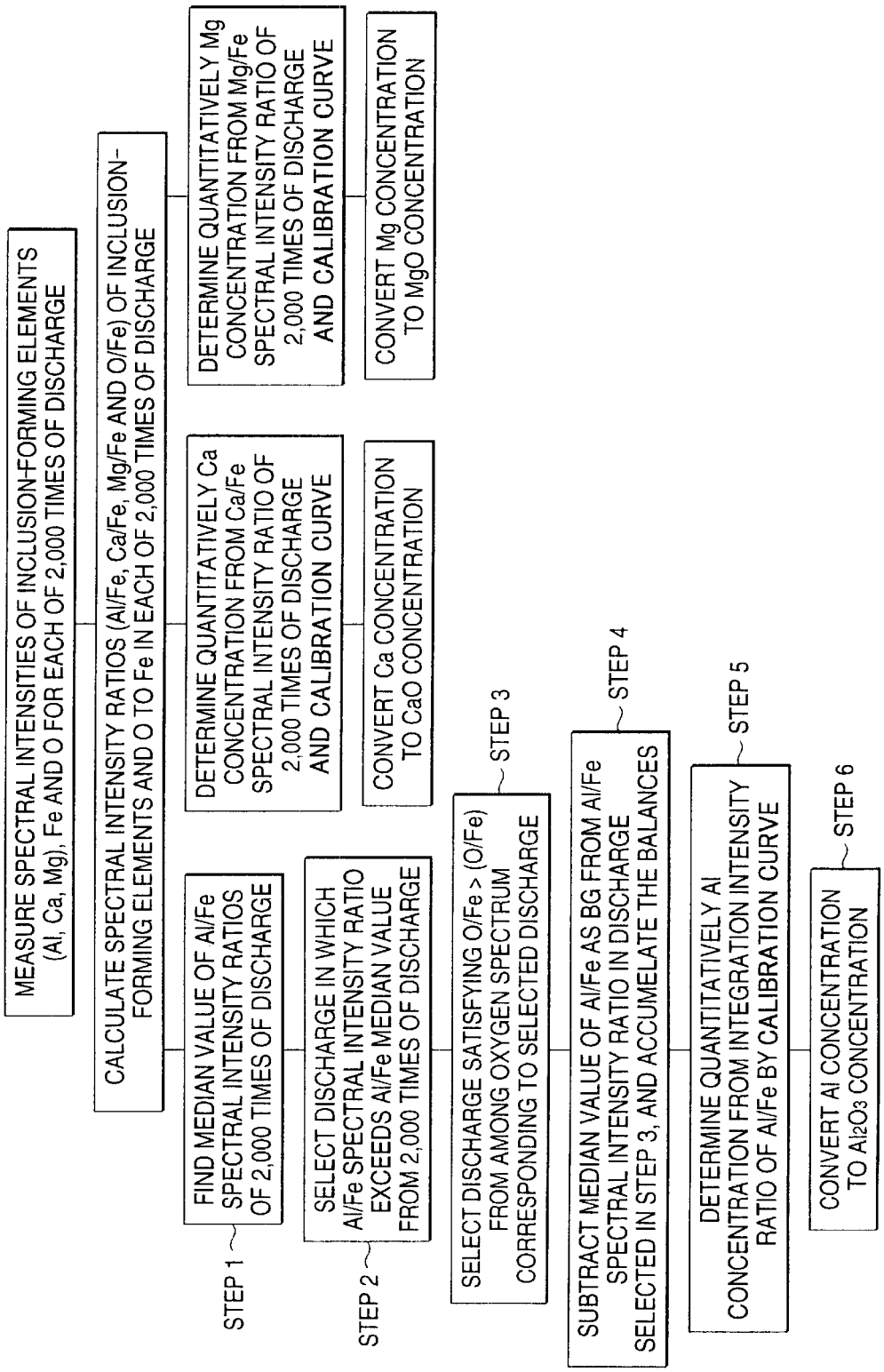
FIG. 6 is a flowchart showing typically a procedure when a quantitative determination method by a conventional emission spectral analysis method and a quantitative determination method of oxide-forming elements according to the present invention are used in combination when the oxide elements to be determined quantitatively contain solid insoluble elements.

Ca and Mg dissolve only in the order of ppm or ppb in the matrix Fe. In the case of so-called "solid insoluble" elements having an extremely small dissolution concentration in the matrix, comparison with the predetermined intensity that represents the dissolution concentration may be omitted from the operation described above. When the presence of solid soluble Al and solid insoluble Mg and Ca is expected as the oxide-forming elements in a material containing Fe as the matrix, for example, the method of the present invention can be employed in combination with the conventional method that does not compare the dissolution concentration as the predetermined intensity, as shown in FIG. 6.

Needless to say, the method of the present invention can execute not only the quantitative determination but also the qualitative determination. Among others, a composition of one inclusion can be determined both qualitatively and quantitatively when the spectrum for each discharge is analyzed as shown in FIG. 1. Therefore, when such an analysis is carried out for a plurality of inclusions and the results are processed statistically, the composition types of the inclusions can be classified.

Although the description given above mainly deals with the case of the iron matrix, the present invention can be applied naturally to the analysis of other melt materials of other metals such as aluminum.

EXAMPLE 1

Molten steel was collected from inside a converter during a steel making step in a steel making process and was solidified in a mold to give an analysis specimen. The oxygen concentration of the specimen was quantitatively determined by the method of the present invention. The procedure of the quantitative determination is shown in FIG. 3.

Figure 3:
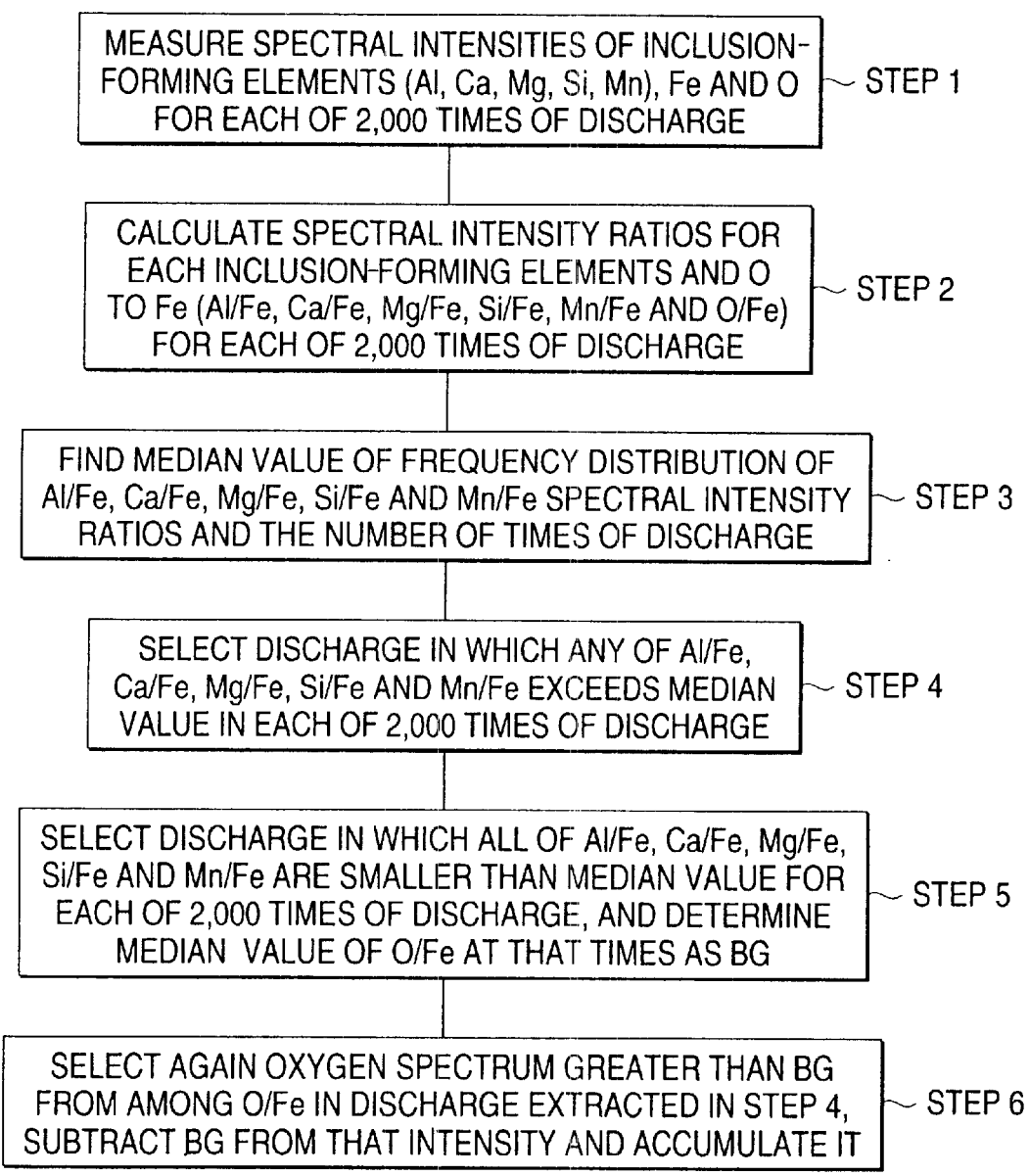
FIG. 3 is a flowchart showing typically a procedure for a quantitative determination of an oxygen concentration according to the present invention.
Figure 4:
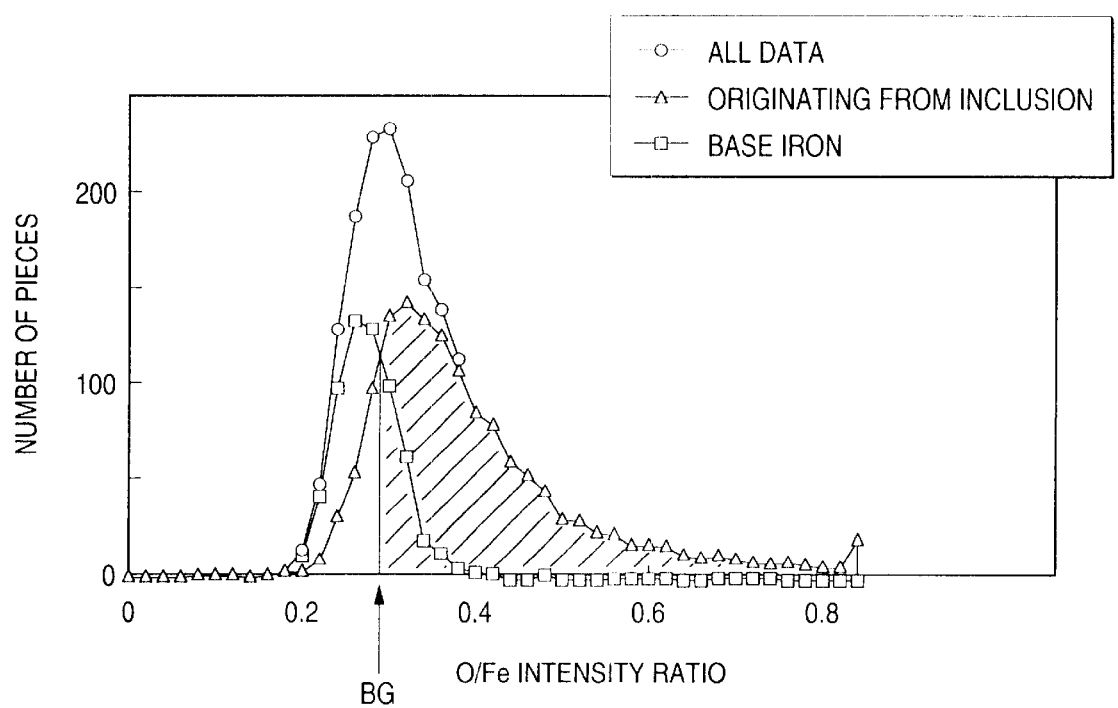
FIG. 4 is a graph showing typically the data acquired by isolating the discharge resulting from inclusions and base iron in the present invention.

FIG. 4 shows the frequency distribution of O/Fe spectral intensity ratios determined by the procedure shown in FIG. 3. A circle in FIG. 4 represents the total spectral intensity of 0OFe obtained by step 2 in FIG. 3, a triangle represents O/Fe spectral intensity ratio originating from the oxide type inclusions and obtained by step 4, and a square represents O/Fe that was obtained by step 5 that was smaller than the median value and was judged as originating from the base iron. It can be seen that the spectral intensity ratios resulting from the oxide and from the base iron were separated from one another.

A calibration curve was prepared using a specimen the oxygen concentration of which was known by the chemical analysis. Then, the oxygen concentration was quantitatively determined for each of ten analysis specimens. The result is tabulated in Table 1.

Table 1 shows also the analysis values obtained by a combustion-infrared absorption method as a conventional quantitative determination method. It can be appreciated that the values obtained by the method of the present invention were in good agreement with the values obtained by the conventional method. According to the method of the present invention, the time from the arrival of the specimens till the completion of the analysis was 3 minutes. In other words, the analysis of oxygen in the metallic specimen, that had not been made in the past by the optical emission spectroscopic analysis, could be made quickly and accurately in the same way as other elements.

Incidentally, though the median value was used as the predetermined intensity in this embodiment, similar results could be obtained when the mean value or the [mean value+2×standard deviation] was used, too.

Embodiment 2

Figure 5:
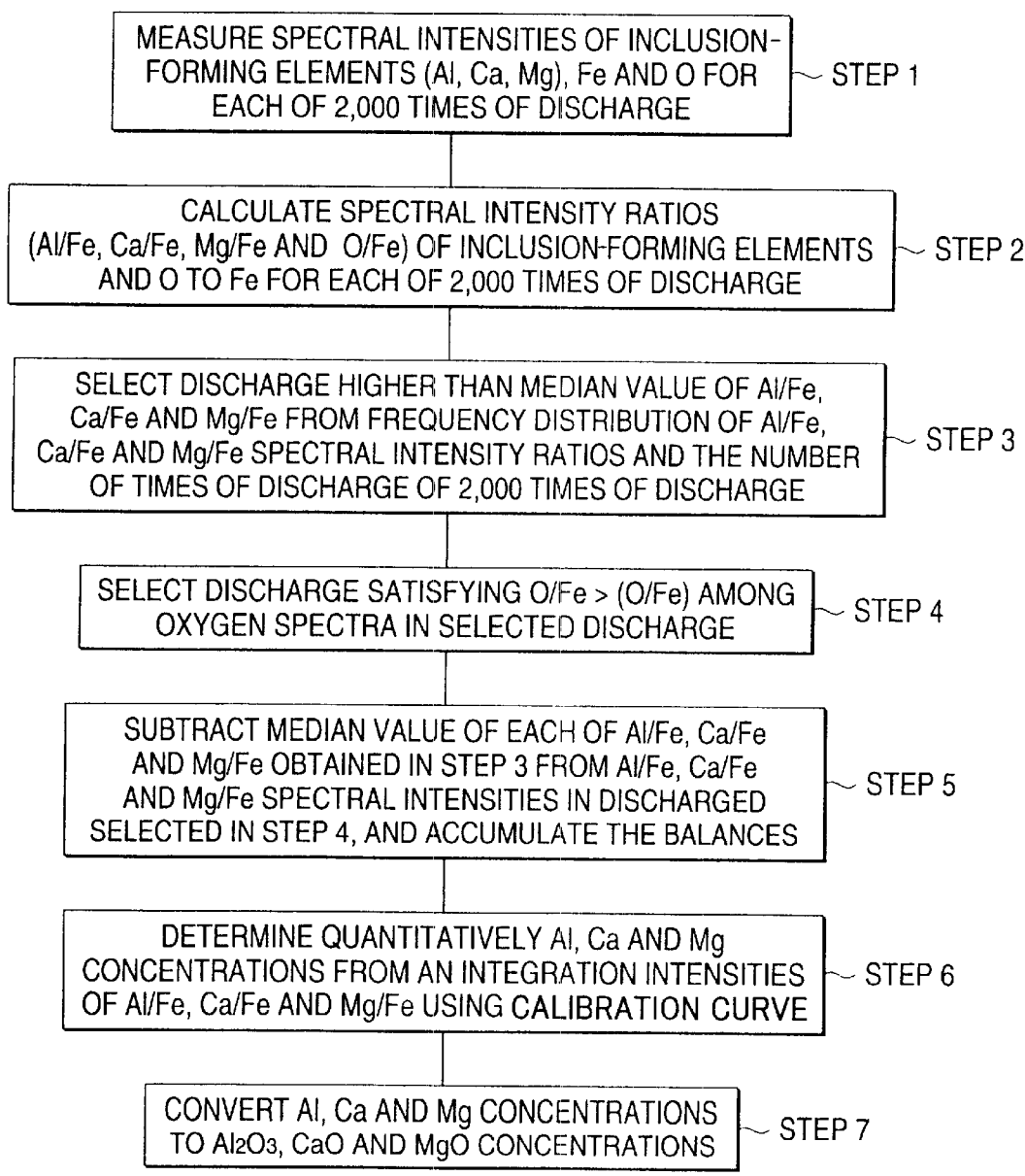
FIG. 5 is a flowchart showing typically a procedure for executing a quantitative determination method of oxide-forming elements according to the present invention.

Molten steel was collected from inside a converter during a steel making step of a steel making process and was solidified in a mold to give an analysis specimen. Composition ratios of $Al_2O_3$, CaO and MgO contained in each specimen were determined by the composition ratio analysis method of oxide-forming elements in oxides according to the present invention. FIG. 5 shows the procedure of this analysis.

Incidentally, the specimens were of four kinds, i.e., A, B, C and D, that were collected from different molten steels. For comparison, the analysis was also carried out for the same specimen by the conventional analysis method (extraction separation—ICP analysis method described above).

Table 2 shows the results of the analysis. It can be appreciated from Table 2 that the values obtained by the analysis method of the present invention were in good agreement with the values obtained by the conventional method. The time from the arrival of the specimens till the completion of the analysis was 3 minutes in the analysis method according to the present invention. This was much shorter than the extraction separation—ICP analysis method according to the prior art that required analysis time of one to two days. Therefore, this method is expected to be advantageously utilized for process control.

TABLE 1

Unit: ppm

| Steel kind | Sample No. | This Invention | Prior art method |
|---|---|---|---|
| A | a | 23 | 25 |
|   | b | 33 | 33 |
|   | c | 70 | 66 |
|   | d | 126 | 130 |
| B | e | 33 | 31 |
|   | f | 44 | 50 |
|   | g | 30 | 30 |
|   | H | 33 | 33 |
|   | I | 24 | 26 |
|   | J | 43 | 41 |

TABLE 2

Unit: wt %

| Sample No. | This Invention | | | Prior art method | | |
|---|---|---|---|---|---|---|
|  | $Al_2O_3$ | CaO | MgO | $Al_2O_3$ | CaO | MgO |
| A | 0.003 | 0.0008 | 0.0005 | 0.002 | <0.0005 | <0.0005 |
| B | 0.004 | 0.0004 | 0.0005 | 0.005 | <0.0005 | <0.0005 |
| C | 0.003 | 0.0008 | 0.0001 | 0.003 | <0.0005 | <0.0005 |
| D | 0.003 | 0.0005 | 0.0006 | 0.003 | <0.0005 | <0.0005 |

Industrial Applicability:

As described above, the present invention makes it now possible to determine far more quickly the oxygen concentration and/or the oxide compositions in the metallic specimen than the prior art method. Therefore, when the present invention is applied to a multi-element simultaneous determination type optical emission spectrometer in order to execute the component analysis for operation control simultaneously with the oxygen analysis and/or the oxide composition analysis, the present invention can improve efficiency of the analysis work, increase yield in the refining process and reduce the production cost.

What is claimed is:

1. A method of quantitatively determining mean oxide-forming element concentrations originating from oxides in a metallic material, the method comprising the steps of:

(1) conducting a discharge operation a plurality of times between said metallic material and an opposing electrode in an inert gas atmosphere to obtain emission spectra;

(2) selecting from said spectra the discharge by which an oxide-forming element spectrum and an oxygen spectrum exceed predetermined respective intensities;

(3) subtracting said predetermined intensity of said oxide-forming elements as a background from the intensity of said oxide-forming element spectrum in said selected discharge, and accumulating spectra balances to obtain a cumulative spectral intensity; and (4) executing quantitative determination using a calibration curve, of the oxide-forming element concentration originating from oxides and said cumulative spectra intensity, prepared separately.

2. The method of quantitatively determining mean oxide-forming element concentrations originating from oxides in a metallic material, according to claim 1, wherein at least one of the following; median value, mean value, or mean value+n×standard deviation (n: positive integer) in a frequency distribution of spectral intensity and the number of discharges is used as said predetermined intensity.

3. The method of quantitatively determining mean oxide-forming element concentrations originating from oxides in a metallic material, according to claim 1, wherein the spectral intensity of the element to be determined quantitatively is converted to an intensity ratio with a matrix element of said metallic material.

4. The method of quantitatively determining mean oxide-forming element concentrations originating from oxides in a metallic material, according to claim 1, wherein the spectral intensity of the element to be determined quantitatively is converted to an intensity ratio with the spectral intensity of a matrix element of said metallic material, and said predetermined intensity is at least one of the following; median value, mean value or mean value+n×standard deviation (n: positive integer) in a frequency distribution of said spectral intensity ratio of said element to be determined quantitatively for a number of discharges.

5. The method of quantitatively determining mean oxide-forming element concentrations originating from oxides in a metallic material, according to claim 1, wherein said metallic material is iron.

6. A method of quantitatively determining a mean oxygen concentration in a metallic material comprising the steps of:

(1) conducting a discharge operation a plurality of times between said metallic material and an opposing electrode in an inert gas atmosphere to obtain emission spectra;

(2) selecting the discharge in which an oxide-forming element spectrum exceeds a predetermined intensity;

(3) selecting oxygen spectra obtained by said discharge;

(4) determining a background of the oxygen spectra from a frequency distribution of the intensity of the oxygen spectra and the number of discharges in the oxygen spectra other than the oxygen spectra selected by the step (3);

(5) selecting again the oxygen spectra having intensity higher than said background from among the oxygen spectra selected by the step (3);

(6) subtracting said background from the intensity of the oxygen spectra selected again, and obtaining a cumulative spectral intensity of oxygen by accumulating spectra balances; and (7) executing quantitative determination using a separately prepared working curve of oxygen concentration and cumulative spectral intensity.

7. The method of quantitatively determining a mean oxygen concentration in a metallic material according to claim 6, wherein at least one of the following; median value, mean value, or mean value+n×standard deviation (n: positive integer) in a frequency distribution of spectral intensity and the number of discharges is used as said predetermined intensity.

8. The method of quantitatively determining a mean oxygen concentration in a metallic material according to claim 6, wherein the spectral intensity of the element to be determined quantitatively is converted to an intensity ratio with a matrix element of said metallic material.

9. The method of quantitatively determining a mean oxygen concentration in a metallic material according to claim 6, wherein the spectral intensity of the element to be determined quantitatively is converted to an intensity ratio with the spectral intensity of a matrix element of said metallic material, and said predetermined intensity is at least one of the following; median value, mean value or mean value+n×standard deviation (n: positive integer) in a frequency distribution of said spectral intensity ratio of said element to be determined quantitatively for a number of discharges.

10. The method of quantitatively determining a mean oxygen concentration in a metallic material according to claim 6, wherein said metallic material is iron.

* * * * *